US005705153A

United States Patent [19]

Shorr et al.

[11] Patent Number: 5,705,153
[45] Date of Patent: Jan. 6, 1998

[54] GLYCOLIPID ENZYME-POLYMER CONJUGATES

[75] Inventors: Robert G. L. Shorr, Edison; Carl W. Gilbert, Basking Ridge, both of N.J.; Brian M. Martin, Rockville, Md.; Myung-Ok Cho, Seoul, Rep. of Korea; Edward J. Ginns, Bethesda, Md.

[73] Assignee: The United States of America, as represented by The Department of Health and Human Services, Washington, D.C.

[21] Appl. No.: 735,961

[22] Filed: Oct. 23, 1996

Related U.S. Application Data

[60] Division of Ser. No. 346,680, Nov. 30, 1994, Pat. No. 5,620,884, which is a continuation-in-part of Ser. No. 989,802, Dec. 10, 1992, abandoned.

[51] Int. Cl.⁶ .................. A61K 38/47; C12N 9/96; C12N 9/42
[52] U.S. Cl. .................. 424/94.61; 424/94.3; 435/188; 435/209
[58] Field of Search .................. 424/94.61, 94.3; 435/188, 209

[56] References Cited

U.S. PATENT DOCUMENTS

| 3,910,822 | 10/1975 | Pentcher | 435/200 |
|---|---|---|---|
| 4,179,337 | 12/1979 | Davis et al. | 435/181 |
| 4,749,570 | 6/1988 | Poznansky | 435/188 |
| 4,935,465 | 6/1990 | Garman | 525/54.1 |
| 5,122,614 | 6/1992 | Zalipsky | 548/520 |

FOREIGN PATENT DOCUMENTS

| WO8905850 | 6/1989 | WIPO . |
|---|---|---|
| WO9007573 | 7/1990 | WIPO . |
| WO9213067 | 8/1992 | WIPO . |

OTHER PUBLICATIONS

Drugs 44(1):72–93 1992.
Nucci, et al. Advanced Drug Delivery Reviews. 6 (1991) 133–151.
Barton, et al. New England Journal of Medicine vol. 324 No. 21, pp. 1464–1470 (May 1991).
New England Journal of Medicine vol. 328 No. 21 pp. 1566–1567; Letters to the Editor (May 1993).
Dawson, et al. The Journal of Biological Chemistry vol. 245 No. 2 Issue of Jan. 25, 1970 pp. 410–416.
Herschfeld, et al. New England Journal of Medicine vol. 316 No. 10 pp. 589–596 (Mar. 1987).
Herschhom, R. New England Journal of Medicine vol. 316 No. 10 pp. 623–624 (Mar. 1987).
Enzyme Replacement In Genetic Diseases, Grabowski, et al. pp. 167–208 of *Enzymes as Drugs* Edited by John S. Holcenberg and Joseph Roberts, 1981 John Wiley & Sons, Inc.

*Primary Examiner*—Rebecca E. Prouty

[57] ABSTRACT

Conjugates containing glucocerebrosidase and non-antigenic polymers such as polyethylene glycol are disclosed. The conjugates circulate for extended times and have prolonged activity in vivo when compared to unmodified enzymes. The conjugates are useful in the treatment of Gaucher's Disease and have improved enzyme activity at the pH ranges associated with lysosomal, arterial and capillary regions.

10 Claims, No Drawings ns is a division of application Ser. No. 08/346,680, filed Nov. 30, 1994, which application is now U.S. Pat. No. 5,620,884, which is a continuation-in-part of U.S. patent application Ser. No. 07/989,802 filed Dec. 10, 1992 now abandoned.

GLYCOLIPID ENZYME-POLYMER CONJUGATES

This application is a division of application Ser. No. 08/346,680, filed Nov. 30, 1994, which application is now U.S. Pat. No. 5,620,884, which is a continuation-in-part of U.S. patent application Ser. No. 07/989,802 filed Dec. 10, 1992 now abandoned.

BACKGROUND OF THE INVENTION

The present invention relates to conjugates having prolonged hydrolyzing activity in vivo against glycolipids such as glucocerebroside.

Gaucher's Disease is an autosomal recessive genetic disorder which effects about 20,000 people in the Unites States. The disease is the most common lysosomal storage disorder and describes a defect in the afflicted's naturally-occurring glucocerebrosidase (GC). This defect causes pathological storage of the complex lipid, glucocerebroside, primarily in organs and tissues of the reticuloendothelial system. The disease is systemic and patients may experience enlargement of the liver and spleen as well as replacement of the bone marrow with lipid-filled cells known as Gaucher cells.

Unfortunately, there is currently no cure for patients suffering from this disease. Treatment for the disease is largely symptomatic. For example, analgesics are used for relief of pain, blood and platelet transfusions are often indicated. In cases where the disease is severe, a splenectomy is indicated to remove the enlarged spleen.

Gaucher's Disease is considered to be a good candidate for enzyme-replacement therapy. For example, U.S. Pat. No. 3,910,822 discloses the use of GC isolated from human placental tissue as a treatment of Gaucher's Disease. In addition, PCT Publication Nos. WO 90/07573 and WO 89/05850 describe preparing GC using recombinant DNA techniques. While these advancements are significant, effective treatment and management of the disease for many patients remains elusive. A chief drawback with current therapies is the relatively short period of time that the replacement enzyme is active in vivo. Accumulated glucocerebroside is not always fully metabolized. Thus, the long term effects of the lingering glycoprotein has not been addressed.

U.S. Pat. No. 4,935,465 describes protein conjugates including glucocerebrosidase reversibly linked to water soluble polymers. The linking groups described therein are based on maleic acid derivatives which are quickly hydrolyzed in vivo and thus release the unmodified protein from the polymer. The present inventors, however, have found that alternative linking groups having a much greater resistance to in vivo hydrolysis provide conjugates which are enzymatically-active over longer periods and thus are better suited to act on accumulated glycolipids and thus reduce the residual amounts of glucocerebroside in the plasma and normalize spleen, liver and skeletal abnormalities.

In spite of the recombinant enzyme's apparent homology with human enzymes, one shortcoming is the fact that recombinantly prepared GC has been found to have low levels of activity at lysosomal pH levels which tend to be from about 4.0 to 5.0. For example, it has been determined that some recombinantly prepared GC have activity levels of only 10% at pH 4.0 and 30% at pH 4.5 (where activity at the optimal pH of about 5.5 is defined as 100%). In view of the fact that Gaucher's Disease is a lysosomal storage disorder, improving the activity of a recombinant enzyme at lower pH's would be a significant advance. Yet another shortcoming associated with recombinantly prepared GC is its suboptimal activity at pH ranges associated with arterial and capillary regions, typically about 7.4±0.5. Any increase in enzyme activity of exogenous enzyme replacements would enhance treatment.

SUMMARY OF THE INVENTION

The present invention provides biologically active conjugates having prolonged activity against glycolipids such as glucocerebroside. The conjugates contain a substance such as an enzyme or enzyme fragment having the ability to hydrolyze glycolipids and a substantially non-antigenic polymeric substance. In one preferred aspect of the invention, the conjugates include glucocerebrosidase or a substance having glucocerebrosidase activity covalently attached to an activated form of a polyalkylene oxide such as polyethylene glycol. In this regard, the polymer will have a molecular weight of from about 1,000 to about 90,000.

The present invention also provides methods of preparing the conjugates. The methods include reacting a substance having activity against glycolipids with a substantially non-antigenic polymeric substance under conditions sufficient to effect conjugation of the substituents while maintaining at least a portion of the anti-glycolipid activity. Such conditions include reacting the polymer with the enzyme-like substance in molar ratios ranging from about 5:1 to 125:1. The resultant conjugates have from about 1 to 25 polymeric strands attached to each molecule of enzyme-like substance.

The invention also provides methods of treating Gaucher's Disease. In this aspect of the invention, treatment includes administering an effective amount of the conjugates described herein to patients or mammals requiring such therapy.

As a result of the present invention, conjugates having substantially prolonged enzyme-like activity against glycolipids in vivo are provided. The conjugates are substantially resistant to in vivo hydrolysis and thus uniquely allow less frequent administration of the therapeutic conjugate when compared to unmodified enzyme preparations and prolonged activity against accumulated glycolipids.

More importantly, it has been surprisingly found that recombinant glucocerebrosidase-poly(alkylene oxide) conjugates in certain embodiments have an unexpected increase in activity at the pH ranges associated with lysosomal and circulatory regions.

For a better understanding of the present invention, reference is made to the following description and its scope will be pointed out in the appended claims.

DETAILED DESCRIPTION OF THE INVENTION

The conjugates include substances having the ability to hydrolyze glycolipids. Such substances preferably have a glucocerebrosidase or glucocerebrosidase enzyme-like activity. These substances can be prepared or obtained from a variety of sources, including recombinant or mammalian extracted GC. It is preferred that the enzyme included in the conjugate be prepared using recombinant techniques. In this regard, the recombinantly prepared glucocerebrosidase such as that disclosed in PCT WO 89/05850 may be used herein. The contents of this PCT publication are hereby incorporated by reference. Alternatively, glucocerebrosidase may be obtained from mammalian sources such as human placental tissue as disclosed in U.S. Pat. No. 3,910,822. It is to be understood that other substances including pro-enzymes and fractions of enzymes or pro-enzymes can also be included in the conjugates of the present invention. As used herein, the expression "the ability to hydrolyze glycolipids" means any substance which demonstrates in vivo activity against mammalian glycolipids especially glucocerebroside. These substances are prepared by using techniques known to those of ordinary skill in the art such as tissue culture, extraction from plant or animal sources or by recombinant DNA methodologies. Transgenic sources of enzymes, pro-enzymes and fractions thereof are also contemplated. Such materials are obtained from transgenic animals, i.e. mice, pigs, cows, etc. wherein the enzyme is expressed in milk, blood, or tissues. Catalytic antibodies specific for glycolipid catalysis are also contemplated. Such antibodies can be prepared using recombinant technologies where antibodies specific to a glycolipid binds to the glycolipid and cleaves the CHO-lipid bond. The method by which the enzymatic substance is prepared for the conjugates of the present invention is not limited to those described herein.

The substantially non-antigenic polymer substances included in the conjugates are preferably poly(alkylene oxides). Within this group of substances are alpha-substituted polyalkylene oxide derivatives such as monomethoxypolyethylene glycols (mPEG's) or other suitable alkyl substituted derivatives such as $C_1$-$C_4$ alkyl groups. It is preferred, however, that the non-antigenic material be a monomethyl-substituted PEG homopolymer. Alternative polymers such as other polyethylene glycol homopolymers, polypropylene glycol homopolymers, other alkyl-polyethylene oxides, bis-polyethylene oxides and co-polymers or block co-polymers of poly(alkylene oxides) are also useful. In those aspects of the invention where PEG-based polymers are used, it is preferred that they have molecular weights of from about 1,000 to about 90,000.) Molecular weights of about 2,000 to 50,000 are preferred and molecular weights of from about 2,500 to about 12,5000 are especially preferred.

Alternative non-antigenic polymeric substances include materials such as dextran, polyvinyl pyrrolidones, polysaccharides, starches, polyvinyl alcohols, polyacryl amides or other similar non-immunogenic polymers. Those of ordinary skill in the art will realize that the foregoing is merely illustrative and not intended to restrict the type of non-antigenic polymeric substances suitable for use herein.

As stated above, covalent modification of the enzyme-like material is preferred to provide the hydrolysis-resistant conjugate. The covalent modification reaction includes reacting a substance having the desired activity against glycolipids with a substantially non-antigenic polymeric substance under conditions sufficient to effect conjugations while maintaining at least a portion of the hydrolyric activity against glycolipids.

The polymers are preferably activated in order to effect the desired linkage with the enzymatically-acting substance. By activation, it is understood by those of ordinary skill in the art that the polymer is functionalized to include a desired reactive group. See, for example U.S. Pat. Nos. 4,179,337 and 5,122,614 which are incorporated by reference herein. In these disclosures, one or both of the hydroxyl-end groups of polyalkylene glycols is converted (and activated) into a reactive functional group. One particularly preferred activated form of PEG for use in the present invention is poly(ethylene glycol)-N-succinimide carbonate. This activated polymer forms stable, hydrolysis-resistant carbamate (urethane) linkages with amino groups of the enzymatically active materials. Isocyanate-activated PEG's as well as cyclic imide thione, aryl imidate, azlactone and the like activated polymers are also of use. While the references incorporated herein describe epsilon amino group modifications of lysine, other conjugation methods are also contemplated. Carbohydrate and/or acid group or other amino acid modifications are also within the scope of the present invention. Covalent linkage by any atom between the enzyme and polymer is possible. Moreover, non-covalent conjugation such as lipophilic or hydrophilic interactions are also contemplated.

The process of the present invention includes preparing or providing the activated polymer and thereafter reacting it with a substance such as recombinant glucocerebrosidase under conditions which allow conjugation without substantial loss of enzyme activity. The reaction is carried out in a buffer such as 0.1M phosphate buffer at a pH of from about 6.0 to about 8.0. The polymer is typically present in a several-fold molar excess over the enzymatic substance. The polymeric excess will range from about 5 to about 125 fold molar excess and is preferably about a 50 to about a 120-fold molar excess. The reaction is carried out at temperatures of from about 0° to 25° C. over time periods ranging from a few minutes to as long as 12 hours. Temperatures of from about 20° to about 25° C. are preferred and time periods of around 1 hour are sufficient to carry out the conjugation reaction.

Following the conjugation reaction, the desired product is recovered using known techniques and purified using column chromatography or similar apparatus if necessary. Depending upon the reaction conditions, the conjugates have from about 1 to about 25 polymeric strands attached to the enzyme-like substance. By controlling the molar excess of the polymer reacted with the enzyme, for example, the artisan can tailor the number of polymeric strands attached. Conjugates containing from about 5 to about 20 polymeric strands are preferred while conjugates containing from about 7 to 18 polymeric strands are most preferred.

In yet another aspect of the invention, there are provided glucocerebrosidase conjugates having improved enzyme activity at pH ranges associated with the lysosomal environment as well as the arterial and capillary regions. Conjugates prepared in accordance with the present invention have unexpectedly been found to have higher levels of enzyme activity than unmodified glucocerebrosidase at pH ranges of from 4.0 to 5.0, which are associated with the lysosomal environment, and from 6.5 to 7.5, which are associated with the arterial and capillary regions.

This higher level of activity was found in spite of polymeric conjugation. Until this time, it had been generally accepted that conjugation reactions reduced or even eliminated biological activity for targeted enzymes, proteins and the like. The enhanced activity in both the pH ranges described above represent a clear advance over the prior art.

While applicants are not bound by theory, it is believed that this increased activity has at least two advantages. At lysosomal pH, enzyme-replacement therapies are enhanced because of glycocerebrosidase's natural lysosomal uptake and the fact that Gaucher's Disease is a lysosomal storage disorder. Secondly, the additional activity observed in arterial and capillary region pH's provides further advantages in the treatment of Gaucher's Disease since more glucocerebroside can be broken down in non-lysosomal areas.

It is also believed that such higher levels of enzyme activity in vivo over time serve to provide persistent activity against glucocerebroside. Such activity represents a major advance toward reducing residual glycolipid concentrations in Gaucher's Disease patients. This in turn will help alleviate some of the sequelae associated with later stage Gaucher's Disease such as enlarged spleen, liver and skeletal abnormalities.

Another aspect of the present invention provides methods of treatment for Gaucher's Disease. The method includes administering an effective amount of the compositions described herein to alleviate the Gaucher's Disease symptoms. Those of ordinary skill in the art will realize that the amount of the conjugate used in the method of the present invention will vary somewhat from patient to patient, however, conjugates capable of delivering from about 0.1 IU/kg to about 200+ IU/kg per administration and preferably 2–6 IU/kg are contemplated. The optimal dosing of the conjugate can be determined from clinical experience.

Further in this regard, the amount of the conjugate administered to treat Gaucher's Disease is an amount that is sufficient to significantly reduce pathological glycolipid concentrations in vivo, and, in particular, the glycolipid glucocerebroside. The maximal dosage for humans is the highest dosage that does not cause clinically important side effects.

An important feature however is that by covalently combining the polymeric substance and the glycolipid hydrolyzing substance as described herein, the conjugates are substantially resistant to hydrolysis in vivo. The conjugates thus act on accumulated glucocerebroside in vivo to a greater extent than prior art compositions. Even further, it has been demonstrated that the glucocerebrosidase conjugates described herein have enhanced enzyme activity at pH ranges most associated with maximal treatment for Gaucher's Disease.

EXAMPLES

The following examples serve to provide further appreciation of the invention but are not meant in any way to restrict the effect of the scope of the invention.

EXAMPLE I

Modification of Glucocerebrosidase with SC-PEG

In this example, recombinant glucocerebrosidase was conjugated with the activated poly(ethylene glycol)-N-succinimide carbonate (SC-PEG) described in U.S. Pat. No. 5,122,614. The polymer had a molecular weight of about 5000. The recombinant glucocerebrosidase (rGC) was prepared in accordance with the method described in PCT Publication No. WO 89/05850

Procedures: 1.8 mg of recombinant glucocerebrosidase (rGC) in 92 Mm NaOAc pH 5.8/10% glycerol/18% EtOH was dialyzed with 0.1M Sodium phosphate buffer solution, pH 7.0 using a Centricon-10 (a product of the Amicon Corporation of Beverly, Mass.). The final concentration of the rGC was ~0.5 mg/ml. 18 mg of SC-PEG (10-fold excess by weight=120 molar excess) was added to the enzyme solution and the reaction mixture was stirred for 1 hr. at room temperature. The reaction was quenched by adding 0.1M glycine. The unreacted PEG was removed by dialysis into a buffer solution having a pH of 6.5. The modification was checked by SDS-gel and the enzyme activity was measured by Fluorimeter F-2000 Fluorescence Spectrophotometer, a product of Hitachi, Japan.

Results: The molecular weight of PEG-GC was approximately estimated to be ~120,000–160,000 by SDS-gel. This corresponds to conjugates having about ~12–20 PEG strands attached. The enzyme activity was measured by using the artificial substrate 4-methyl-umbelliferyl-β-D-glucopyranoside (4-MUG) and 90±5% of the GC activity was retained.

EXAMPLE II

Modification of GC with SC-PEG

In this example, the procedure of example I is repeated using that a 20 fold molar excess of SC-PEG and same rGC.

Procedures: 100 mg of rGC is dialyzed with 0.1M phosphate buffer, pH 7.0 using a Minisette (available from Filtron of Northborough, Mass.) to yield a 1 mg/ml solution. To this solution 167 mg of SC-PEG (a 20 fold molar excess) is added and stirred for 1 hr. at room temperature (~20° C.). The reaction stopped by adding a 20 fold molar excess of 0.1M glycine. The unreacted reagents are removed by dialysis using the Miniserie into a 20 millimolar NaOAC/phosphate 0.025% Tween 80 buffer, pH 6.5.

Results: PEG-GC is estimated to have a molecular weight range of about 65,000–95,000 Daltons by SDS-PAGE. This suggests that between 1 and 7 PEG 5000 strands are attached to each enzyme molecule. It is estimated that greater than 80% activity of the GC is retained.

As can be seen from the foregoing example, by varying the amounts of the reactants, the amount of PEG attached to the GC can be varied. This, in turn, will vary the circulating life of the conjugate. Lower modifications yield conjugates with circulating lives substantially longer than native GC but less than the higher modified PEG-rGC made in Example I.

EXAMPLE III

In this example, the circulating half-lives of various glucocerebrosidase products was compared. The circulating half-life of both recombinant GC and PEG-rGC were determined in rats. Six rats about 300±25 gm were used for this experiment. Three rats were injected i.p. with rGC and three were similarly injected with PEG-rGC at a dose of 60 IU/kg. At various time points the rats were bled and plasma prepared. The plasma was stored at 4° C. until assayed. Glucocerebrosidase activity was determined using the 4-MUG fluorescent assay. The half-lives ($T_{1/2}$) are reported in the following table. The half-life for placental GC was reported by Brady, et al, New England Journal of Medicine 291: 990–993 (1974); the half-life of Ceredase™ was reported by Whittington, et al, Drugs 44(1) 72–93 (1992). The results are reported below.

| CIRCULATING HALF-LIVES OF GLUCOCEREBROSIDASE | |
|---|---|
| Preparation | T1/2 |
| Placental GC | 25 minutes |
| Chemically Modified Placental GC (Ceredase ™) | 3–11 minutes |
| Recombinant GC[1] | approx. 1 hr (alpha phase) |
| PEG-rGlucocerebrosidase[2] | 6–7 hours (alpha phase) |

Ceredase™: a product of the Genzyme Corporation
[1]Prepared in accordance with the method of Ginns, et al in PCT WO 89/05850
[2]As prepared in Example I As can be seen from the table, PEG-GC conjugates prepared in accordance with the present invention have a substantially prolonged increase in circulating life when compared to unmodified enzymes.

EXAMPLE IV

In this example, PEG-rGC conjugates were prepared in accordance with Example I by reacting 1.8 mg rGC with 18 mg of SC-PEG. SDS-PAGE determined approximately 9 PEG'S/rGC molecule. These conjugates were compared to unconjugated rGC prepared according to the method of Ginns, et al., supra, to compare the average amount of glucocerebrosidase activity at various pH's which approximate lysosomal, arterial and capillary regions. Optimal activity (100%) was determined at pH optima using standard procedures. At each pH level, an average of four experiments was obtained by normalizing the enzyme activity as determined by the 4-MUG assay described in Example I. Each test tube contained artificial substrate in aqueous system buffered to the desired pH.

The results of the study are set forth in the table below.

| Sample | Average Enzyme Activity pH | | | | | | | |
|---|---|---|---|---|---|---|---|---|
| | 4.0 | 4.5 | 5.0 | 5.5 | 6.0 | 6.5 | 7.0 | 7.5 |
| rGC | 18 | 51 | 72 | 100 | 92 | 61 | 34 | 10 |
| PEG-rGC | 27 | 58 | 73 | 91 | 100 | 75 | 40 | 16 |

Average n = 4

As can be seen from the table, the conjugates provided enhanced activity in the pH ranges most associated with Gaucher's Disease therapy, i.e., lysosomal (pH 4.0–5.0) and arterial and capillary pH's (pH 6.5–7.5). These increases are completely unexpected and contrary to what was expected.

While there have been described what are presently believed to be the preferred embodiments of the present invention, those skilled in the art will realize that changes and modifications may be made thereto without departing from the spirit of the invention. It is intended to claim all such changes and modifications as fall within the true scope of the invention.

What is claimed is:

1. A method of treating Gaucher's Disease comprising administering an effective amount of a glucocerebrosidase conjugate having enhanced enzymatic activity at pH ranges of from about 4.0–5.0 and about 6.5–7.5, comprising recombinant glucocerebrosidase and from about 1 to about 25 poly(alkylene oxide) strands, each strand having a molecular weight of from about 1,000 to about 15,000, and each strand being covalently linked via a urethane linkage to an amino group on said recombinant glucocerebrosidase.

2. The method of claim 1, wherein each of said poly (alkylene oxide)s is terminally substituted with a $C_{1-4}$ alkyl group distal to said recombinant glucocerebrosidase.

3. The method of claim 1, wherein said poly(alkylene oxide) is selected from the group consisting of polyethylene glycol homopolymers, polypropylene glycol homopolymers, alkyl-capped polyethylene oxides, bis-activated polyethylene oxides and copolymers or block copolymers of poly(alkylene oxides).

4. The method of claim 1, wherein said poly(alkylene oxide) has a molecular weight of from about 1,000 to about 12,500.

5. The method of claim 4, wherein said polymer has a molecular weight of from about 2,000 to about 12,500.

6. The method of claim 5, wherein said polymer has a molecular weight of about 5,000.

7. The method of claim 1, wherein about 5 to about 20 poly(alkylene oxide) strands are attached to each molecule of said recombinant glucocerebrosidase.

8. The method of claim 7, wherein about 7 to about 18 poly(alkylene oxide) strands are attached to each molecule of said recombinant glucocerebrosidase.

9. The method of claim 3, wherein said poly(alkylene oxide) is polyethylene glycol.

10. The method of claim 3, wherein said polyethylene glycol is a monomethoxy polyethylene glycol.

* * * * *